US008849424B2

(12) United States Patent
Nippoldt et al.

(10) Patent No.: US 8,849,424 B2
(45) Date of Patent: Sep. 30, 2014

(54) INTEGRATED CONDUCTIVE SENSOR PACKAGE HAVING CONDUCTOR BYPASS, DISTAL ELECTRODE, DISTAL ADAPTER AND CUSTOM MOLDED OVERLAY

(75) Inventors: Douglas D. Nippoldt, Centerville, MN (US); Thomas D. Brostrom, Wayzata, MN (US); Richard J. O'Brien, Hugo, MN (US); Michael A. Schugt, Saint Paul, MN (US); Scott J. Davis, Maple Grove, MN (US); Yaling Fan, Savage, MN (US)

(73) Assignee: Medtronic, Inc., Minneapolis, MN (US)

( * ) Notice: Subject to any disclaimer, the term of this patent is extended or adjusted under 35 U.S.C. 154(b) by 1044 days.

(21) Appl. No.: 12/411,124

(22) Filed: Mar. 25, 2009

(65) Prior Publication Data

US 2009/0248126 A1 Oct. 1, 2009

Related U.S. Application Data

(60) Provisional application No. 61/207,861, filed on Mar. 25, 2008.

(51) Int. Cl.
*A61N 1/00* (2006.01)
*A61N 1/05* (2006.01)
*A61B 5/0215* (2006.01)
*A61N 1/37* (2006.01)
*A61B 5/042* (2006.01)

(52) U.S. Cl.
CPC .............. *A61N 1/056* (2013.01); *A61N 1/3702* (2013.01); *A61B 5/042* (2013.01); *A61B 2562/12* (2013.01); *A61B 5/02158* (2013.01)
USPC .......................................... 607/122

(58) Field of Classification Search
CPC ........... A61N 1/00; A61N 1/05; A61N 1/362; A61B 5/00; A61B 5/215; A61B 5/14; A61B 5/0205
USPC ................. 607/115–116, 119, 122, 125–127, 607/128–131
See application file for complete search history.

(56) References Cited

U.S. PATENT DOCUMENTS

| 4,967,755 | A | * | 11/1990 | Pohndorf ....................... 600/488 |
| 5,535,752 | A | * | 7/1996 | Halperin et al. .............. 600/483 |
| 5,569,883 | A | * | 10/1996 | Walter et al. .................. 174/84 R |
| 5,899,927 | A | | 5/1999 | Ecker et al. |
| 7,087,017 | B2 | | 8/2006 | Christopherson et al. |

(Continued)

FOREIGN PATENT DOCUMENTS

| WO | WO2005058133 | 6/2005 |
| WO | WO2005072817 | 8/2005 |

(Continued)

*Primary Examiner* — Christopher D Koharski
*Assistant Examiner* — Roland Dinga
(74) *Attorney, Agent, or Firm* — Evans M. Mburu

(57) ABSTRACT

This disclosure relates to implantable medical devices (IMDs); in particular, to medical electrical leads having an integrated sensor disposed in a hermetic package and said sensor package accommodates a torque coil and an elongated cable conductor extending therethrough. The integrated sensor can include a pressure sensor, an accelerometer, and the like. The coil and the cable can couple to pacing and sensing electrode coupled to the lead distal to the sensor package. The sensor package is compact, substantially circular in cross section and robust, in that the overall design promote mechanical stability.

22 Claims, 8 Drawing Sheets

(56) References Cited

U.S. PATENT DOCUMENTS

| | | |
|---|---|---|
| 7,254,450 B2 | 8/2007 | Christopherson et al. |
| 7,286,884 B2 | 10/2007 | Marshall et al. |
| 2005/0159800 A1* | 7/2005 | Marshall et al. .............. 607/122 |
| 2006/0264925 A1 | 11/2006 | Sharareh et al. |

FOREIGN PATENT DOCUMENTS

| | | |
|---|---|---|
| WO | WO2005107583 | 11/2005 |
| WO | WO2006069323 | 6/2006 |
| WO | WO2007120884 | 10/2007 |

* cited by examiner

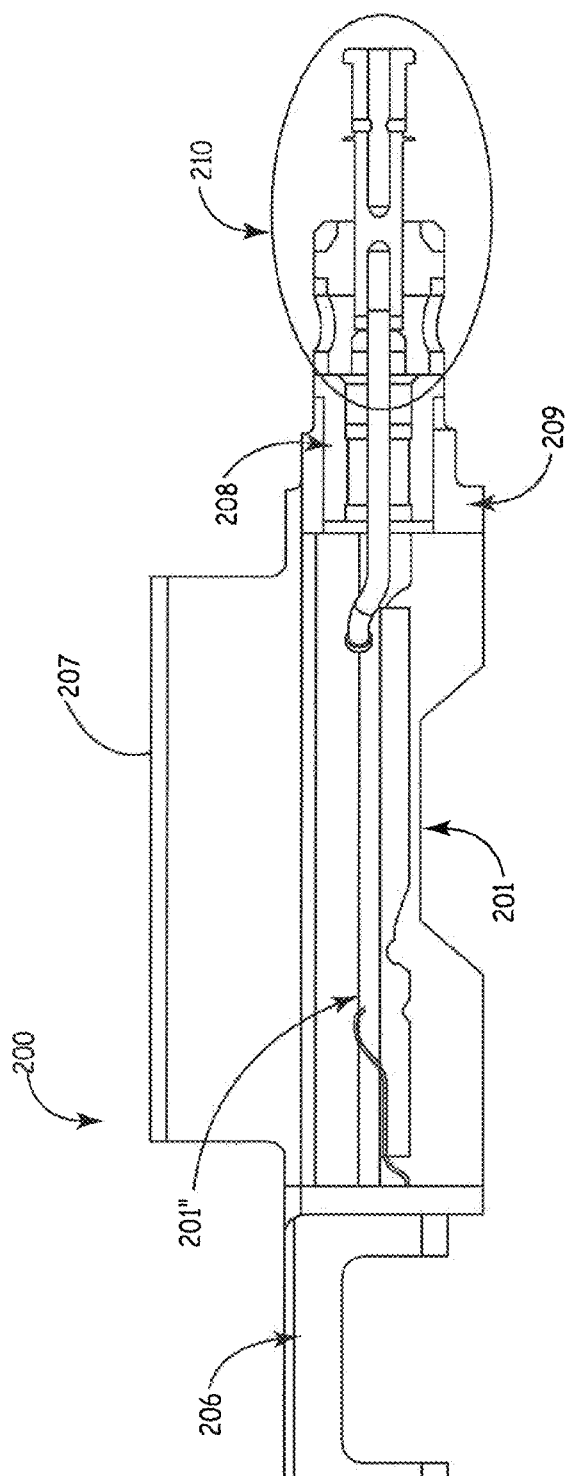
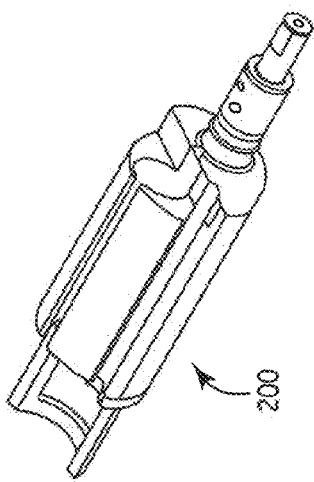
FIG. 4B
FIG. 4A

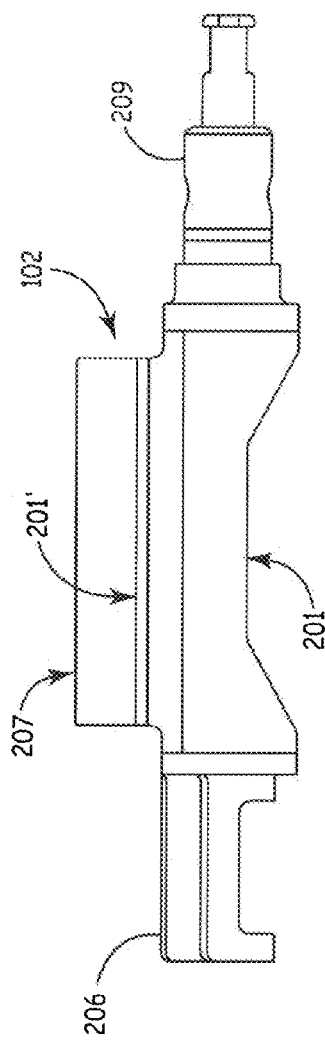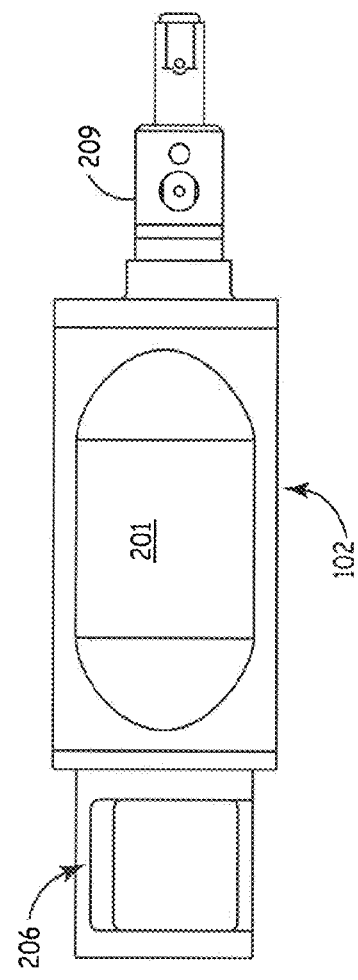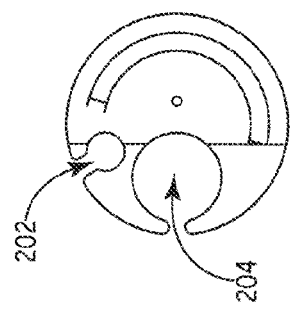
FIG. 6A
FIG. 6B
FIG. 6C

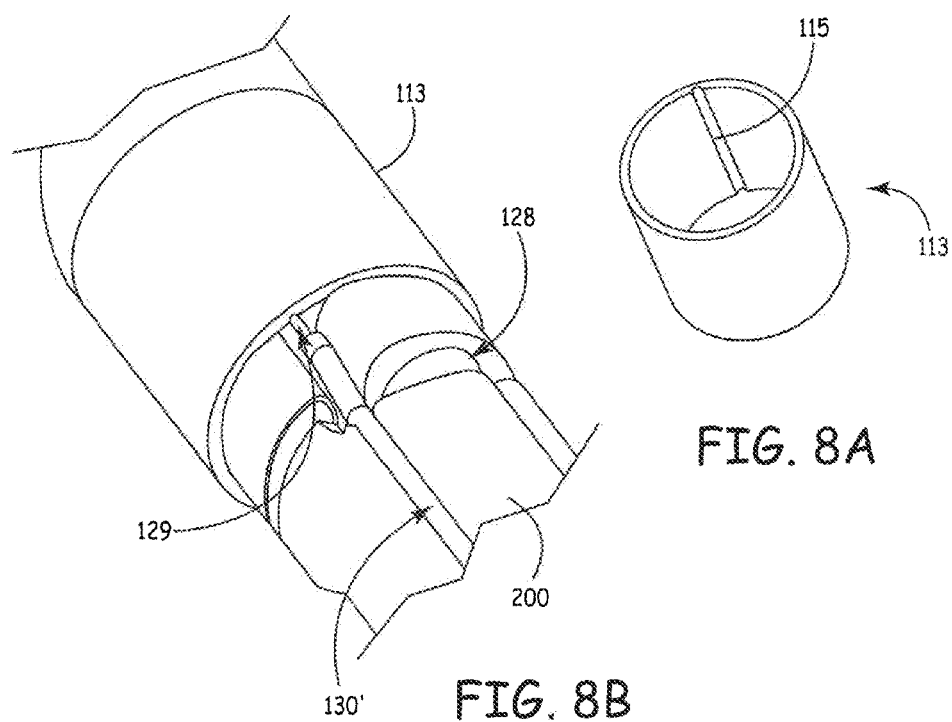

ns, to medical electrical leads coupled to a conductive sensor package, and the package includes at least one integral bypass bore, a pace/sense electrode, a distal adapter, or a custom-molded insulative overlay.

INTEGRATED CONDUCTIVE SENSOR PACKAGE HAVING CONDUCTOR BYPASS, DISTAL ELECTRODE, DISTAL ADAPTER AND CUSTOM MOLDED OVERLAY

RELATED APPLICATION

This application claims the benefit of and priority to U.S. Provisional Application Ser. No. 61/207,861, filed Mar. 25, 2008, entitled, "Integrated Conductive Sensor Package Having Conductor Bypass, Distal Electrode, Distal Adapter and Custom Molded Overlay," the contents of which are incorporated by reference herein in its entirety.

FIELD

This disclosure relates to implantable medical devices (IMDs); in particular, to medical electrical leads coupled to a conductive sensor package, and the package includes at least one integral bypass bore, a pace/sense electrode, a distal adapter, or a custom-molded insulative overlay.

BACKGROUND

Sensors have previously been coupled to cardiac leads. Since the leads are coupled to the myocardium they must possess flexibility and strength. If one or more electrodes are disposed distal to a sensor one or more electrical conductors must pass by the sensor thereby increasing the complexity of the sensor assembly and possibly increasing the dimension of the sensor package.

Since a sensor-bearing lead typically must be fixed in place within or on the heart for consistent sensed signals, an active fixation sub-assembly is often located at the distal tip. Given the closed distal tip and active fixation a stylet is oftentimes used to extend and retract a helical shaped member before torque is applied by a torque coil to fix the helix into adjacent tissue. Thus, the torque coil is a second elongated member, optionally electrically active, that must extend beyond the sensor. In the prior art the cables and coils were simply routed around the sensor module, or package.

For a number of reasons the sensor package of a physiologic sensor must be rendered electrically neutral. This has been accomplished with coating the sensor with insulating material(s) which are oftentimes of inconsistent depth and surface finish. Also, thermoplastic tubing has been used wherein a sensor package is surrounded in a uniform diameter tube of material and it is heat treated to shrink it around the package. This can also result in inconsistent material depth, air bubbles, and the like. Also, due to the thickness of these materials the material covering a transducer portion, such as a sensor membrane, had to be manually removed and replaced with another insulative material (after sealing the edges where the material was removed). Besides the excess time and complexity, the possibility that the numerical yield from this type of production technique can change (i.e., whether beginning at a reasonable yield the yield can vary or drop too low to predict or to make economic sense, respectively).

A need thus exists in the art for compact physiologic sensor packaging that allow stylet delivery, that can reliably convey electrical signals to and from the sensor as well as components coupled distal to the sensor, and that can easily, reliably, and efficiently be rendered electrically neutral (i.e., insulated).

SUMMARY

Thus, herein provided are methods and structures for coupling a conductive sensor package to a distal portion of a medical electrical lead and implant the lead by temporarily inserting a stylet through a portion of the sensor package (to the distal end of the lead). Optionally one or more electrical conductors also pass through a portion of the sensor package without affecting the hermeticity thereof while providing electrical communication with one or more electrodes disposed distal to the sensor. The distal end of the lead can include an active tissue fixation member such as an extendable/retractable or fixed helical screw. Such a screw can be fixed to the distal tip of the lead, thereby requiring rotation via a stylet or of the entire lead to fixate an electrically active distal tip in a desired portion of tissue. The helical screw can be electrically active or neutral whether or not it rotates independently of the lead body or is fixed relative to the lead body. However, if electrically active redundant insulation is applied or utilized to reduce possibility of electrical short circuit or the like. Such a system can be fabricated according to the disclosure with advantages of reduced size, stability, and improved performance characteristics of a manually deployable cardiac sensing and, optionally, therapy delivery lead.

In one embodiment a medical electrical lead is provided which has some or all of the following components. An elongated lead body formed of a biocompatible material having at least one but nominally a pair of longitudinal lumens formed in the lead body. An elongated metallic torque coil disposed within a first lumen of the lead body. An elongated metallic cable disposed within a second lumen of the lead body. A conductive, hermetic sensor package coupled to the lead body and including means for securing a portion of the torque coil and for securing a portion of the cable. With respect to the means for securing the coil and cable, a pair of spaced apart bores align with the longitudinal axis of the lumens of the lead body. One or both bores can be closed bores, partially open bores, and/or essentially fully open channel-like features. In addition, in one embodiment part of the sensor package includes an integral distal adapter member (which forms part of the package) that provides support for components wholly or partially disposed over the package (e.g., a ring electrode) as well as distal to the package (e.g., a flexible distal lead structure that includes a helical screw).

Since the conductive sensor package is typically fabricated of metal, such as titanium alloy or titanium or the like the bores or channels can include electrical insulation intermediate each bore and/or over both the coil and cable. This insulation can be deemed redundant or fault tolerant as the coil and cable are themselves typically insulated. The insulation can include an appropriately sized polymer tube inserted into the bores or channels or placed on the coil and/or cable or a layer of material or equivalent during assembly.

One or more pacing and sensing electrodes can be coupled the lead distal to the sensor package. For instance, the cable can couple to a ring electrode and the torque coil can then couple to a tip-type electrode (e.g., an active fixation helix-type tip electrode). In one embodiment, a ring electrode is integrated with the sensor package, thereby reducing the length of the package. In one form of this embodiment the ring electrode resides entirely within the length of the sensor package. In another form, only a portion of the ring electrode overlies the sensor package.

The sensor package can be used to sense physiologic parameters like pressure and acceleration via one or more deflectable members operatively coupled within the package to circuitry and a communication coil that in turn couples to an IMD.

A method of fabricating a medical electrical lead is also provided whereby an elongated lead body is provided that is formed of a biocompatible material having at least two longitudinal lumens formed in the lead body. Then an elongated metallic torque coil is inserted into a first lumen of the lead body and an elongated metallic cable is inserted into a second lumen of the lead body. The conductive, hermetic sensor system, or package, is then coupled to the lead body, wherein the sensor system includes a deflectable member sensitive to a physiologic variable of a subject, a mechanically robust distal adapter member, a pair of spaced apart metallic (e.g., titanium alloy) bypass structures, and a custom-molded insulative overlay. The metallic torque coil is secured to one of the pair of bypass structures and the elongated metallic cable is secured to the other of the pair of bypass structures. As noted above, electrical insulation should be disposed between each of the pair of bypass structures and the torque coil and the metallic cable, respectively and/or inserted into the bypass structures for added fault tolerance.

In addition, to render the conductive sensor package electrically neutral a custom-molded chemically-treated biocompatible film is first molded, chemically expanded, then slipped over the sensor package, and chemically reduced in diameter for a customized fit. After being reduced in diameter the film includes the topography of all the features of the package including the recessed membrane and diaphragm of the transducer face in only a few simple and efficient processing steps.

The foregoing and other aspects and features will be more readily understood from the following detailed description of the embodiments thereof, when considered in conjunction with the drawings, in which like reference numerals indicate similar structures throughout the several views.

BRIEF DESCRIPTION OF THE DRAWINGS

FIG. 4 is an elevational side view of an exemplary sensor package illustrating an embodiment wherein a relatively thin membrane is used to sense pressure fluctuations on one side of the package and a relatively thicker back portion provides an axis of relative stiffness to the package.

FIGS. 6A, 6B and 6C depict alternate view of the sensor 200 depicted in FIGS. 4 and 5; namely, an elevational side view, a plan view and a cross-sectional view.

FIGS. 8A and 8B are perspective views of an exemplary ring-type electrode 113 used for sensing and pacing and typically disposed distal of the sensor package 200.

DETAILED DESCRIPTION OF THE ILLUSTRATED EMBODIMENTS

In the following detailed description, references are made to illustrative embodiments for methods and apparatus including very small sensors coupled to medical electrical leads. This disclosure provides enhanced mechanical resiliency to very small sensors coupled to medical electrical leads that are cooperatively designed and fabricated.

Figure 1:
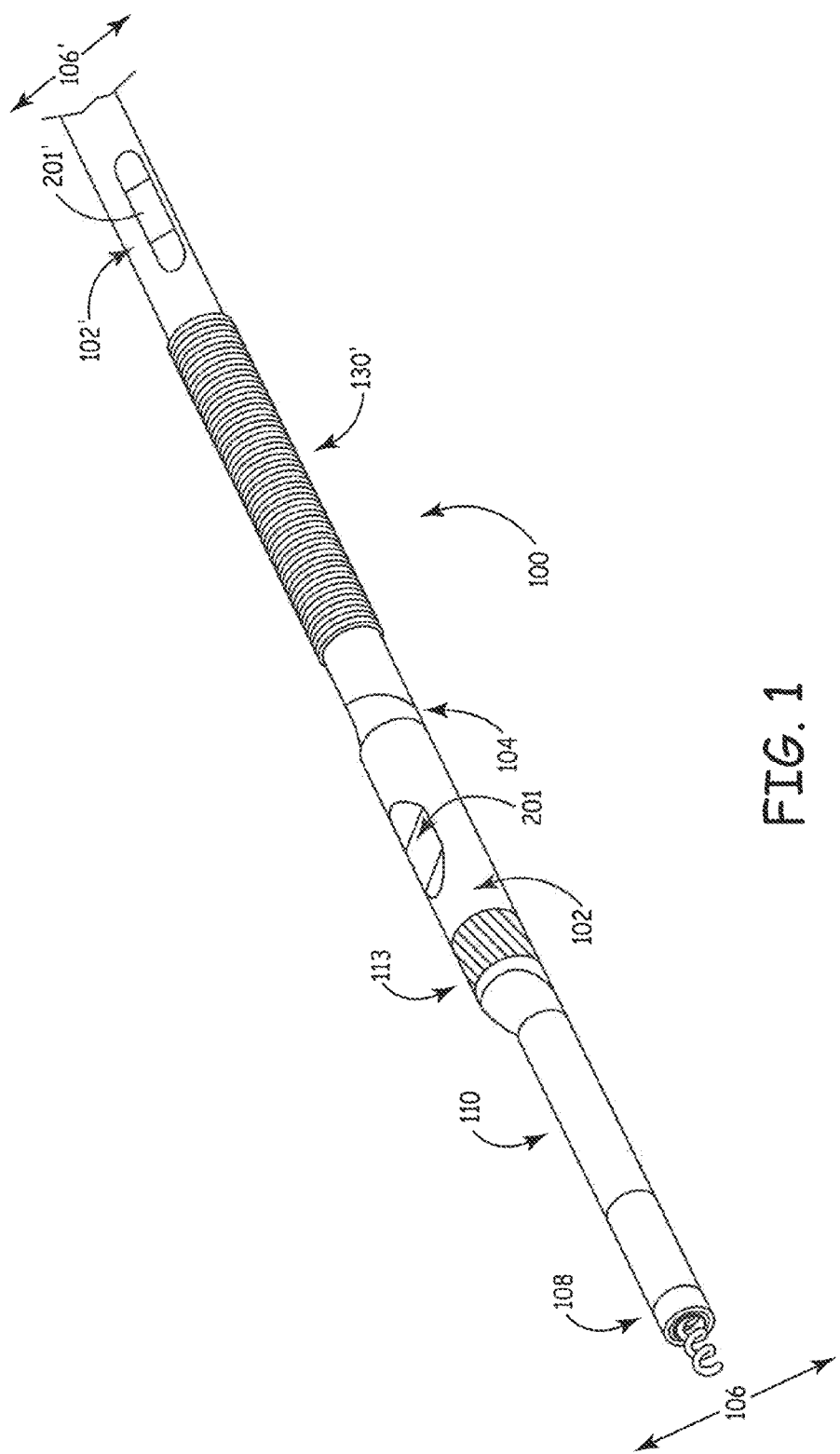
FIG. 1 is a perspective view of the distal portion of a pressure sensing lead body having a pressure sensor with a sensor membrane which deflects due to fluctuations in pressure in a cardiac chamber.

FIG. 1 is a perspective view of the distal portion of a pressure sensing lead body 100 having a pressure sensor 102 with a sensor membrane 201 which deflects due to fluctuations in pressure in a cardiac chamber. In order to best sense such fluctuations, minimize signal artifacts, and limit stress upon the sensor 102, when coupled to myocardial tissue the membrane 201 sweeps laterally (along the axis defined by arrow 106) during chronic implantation. Adjacent to the sensor 102 is optional pacing and sensing ring electrode 113. Coupled to the sensor is a relatively flexible member 110 coupling from the ring electrode 113 to optional extendable and retractable helix sub-assembly 108 used to fixate the tip of lead 100 to adjacent myocardial tissue. A proximal sensor lead portion 104 includes optional right ventricular (RV) coil electrode 130' used for high energy defibrillation therapy delivery. Proximal to the RV coil electrode 130' is an optional second pressure sensor 102' having a sensing membrane 201'. Proximal of the second pressure sensor 102' an optional superior vena cava (SVC) coil electrode (not shown) can be coupled to the lead 100.

Although not depicted in FIG. 1, within the lead body 100 in the proximal sensor lead portion 104 a set of electrical conductors reside within a multi-lumen structure. If the sensor lead 100 is designed only for sensing, two coils will extend at least to the sensor 102. The first, a torque coil, resides in a lumen and is used during implantation (to enhance the so-called "pushability" of the lead 100). The second, a co-axial communication coil resides in a different lumen for carrying signals to and from the circuitry of sensor 102. As noted above, the two coils can be used to establish a desired bending direction for the body of the lead 100 (i.e., laterally to the sensor membrane 201). This desired bending direction results from the slight compressive load placed upon the lead 100 shortly after implantation.

In other configurations, for example if the sensor lead 100 is designed for sensing pressure and cardiac activity and/or pacing a heart, then the torque coil used during implant can be electrically coupled to the tip electrode (e.g., helix of helical sub-assembly 108) and optionally another elongated cable-type conductor can be routed to the ring electrode 113. In this configuration, the desired bending direction remains the same due to the two coils orientation relative to the sensor membrane 201.

Also depicted in FIG. 1 is optional second sensor 102' having a sensor membrane 201' which can have an arbitrary orientation relative to sensor member 201 applying the principles described and depicted herein. That is, in the event that the second sensor 102' is intended to sense pressure within the right atrium (RA) the relative orientation of the two sensors 102,102' can be different or changed during fabrication of the lead 100 to promote a different lateral motion for the sensor 102' (as depicted by arrow 106'). If the second sensor 102' is adapted to sense RA pressures then beside having lateral motion of the membrane 201' relative to the lead 100, the membrane 201' should face away from the nearest wall of the RA. Also, the second sensor 102' can utilize the same digital sensor protocol carried upon the sensor communication bus as the first sensor 102.

Figure 2:
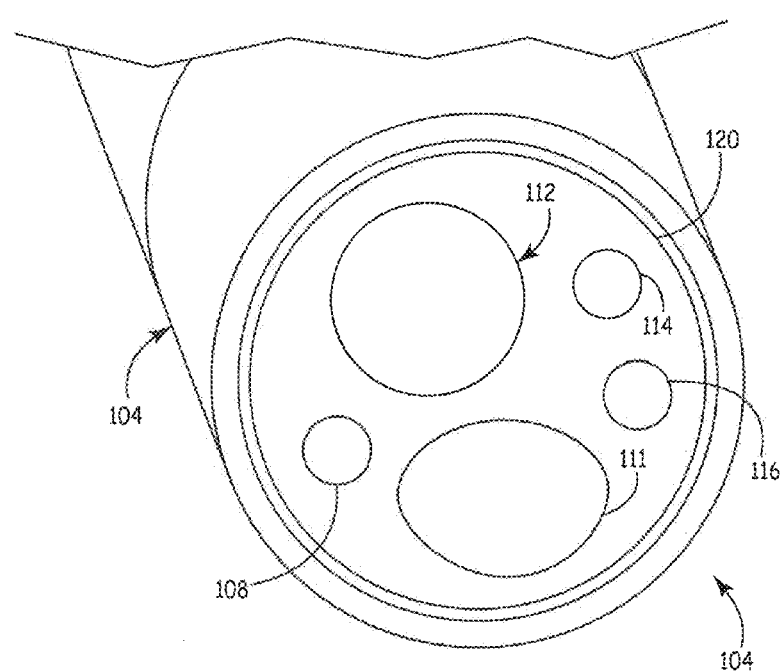
FIG. 2 is a cross-sectional view of a portion of a lead body wherein two major elongated lumens, a sensor lumen and a torque coil lumen are spaced apart and disposed whereby they define a plane which promotes a bending direction perpendicular to the defined plane.

FIG. 2 is a cross-sectional view of a portion of a lead body 104 wherein two major elongated lumens 111,112 (denoted as a sensor bus lumen and a torque coil lumen) are spaced apart and disposed whereby they define a plane through the center axis of each which promotes a desired bending direction perpendicular to the defined plane. As depicted the lead body portion 104 also has three other smaller-diameter lumens 108,114,116 configured to receive an SVC cable, an RV cable, and a ring electrode cable lumen, respectively. The lead body 104 is sheathed in an overlay tubing 110 and the penta-lumen 120 is nominally fabricated of Silicone (e.g., MED-4755 made by Nusil Technology of Carpinteria, Calif.). As depicted the major lumens 111,112 are designed to promote the desired bending direction (indicated generally by arrow 106 of FIG. 3).

Figure 3:
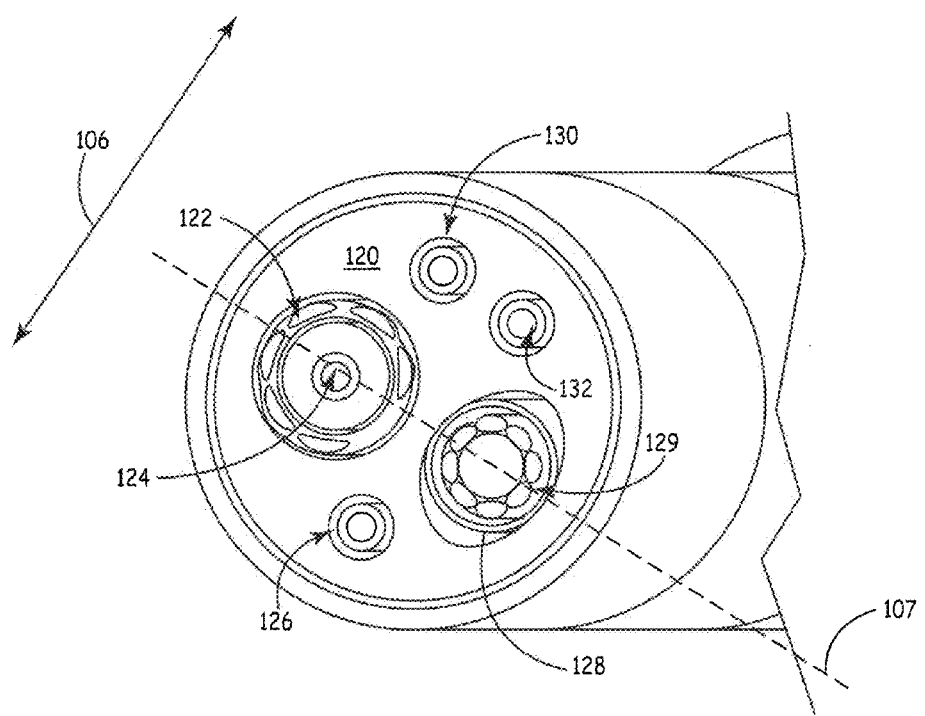
FIG. 3 is a cross-sectional view of the lumens depicted in FIG. 2 and the accompanying components disposed therein; namely, a sensor bus lumen, a torque coil lumen as well as two high energy cables (SVC cable and RV coil) and a low energy pacing cable (ring cable).

FIG. 3 is a cross-sectional view of the lumens depicted in FIG. 2 and the accompanying components disposed therein; namely, an inner sensor bus cable 124 and an outer sensor bus coil 122, a torque coil 129 having an optional covering 128, as well as two high energy cables (SVC cable 126 and RV cable 130) and a low energy pacing and sensing cable (ring cable) 132. The sensor bus coil 122, the sensor bus cable 14, and the torque coil 129 define a plane through the axial center of each (depicted by dashed line 107) and the desired bending direction lies generally perpendicular to this plane (106 in FIG. 3).

FIGS. 4A and 4B depict an embodiment of a sensor package 200 designed and constructed out of titanium according to one form of the invention. For example, a suitable titanium alloy includes Ti 6Al-4V although other alloys and other materials could suffice. FIG. 4A is a perspective view of the package 200 and FIG. 4B is an elevational side view of the sensor package 200 illustrating an embodiment wherein a relatively thin membrane 201 is used to sense pressure fluctuations on one side of the package 200 and a relatively thicker back housing portion 207 provides an axis of relative stiffness to the package 200 (which is generally perpendicular to the package 200 depicted in FIG. 4B (i.e., perpendicular to the drawing sheet). In practice the axis of stiffness is designed so that it is aligned with the desired bending direction 106, 106' of the lead body 104 that is provided by the twin coils described above (and other structures and/or lumens described below in relation to FIGS. 7-10). A distal adapter 206 can is integrated to the sensor package and flexible distal end portion 110 (depicted in FIG. 1) which provides incremental desired bending direction due to the torque coil therein and the proximity to both the rigid sensor package 200 (including distal adapter 206) and the dual-coil proximal lead portion 104. The distal adapter increases the stiffness of the overall package that adds signal accuracy to the output signal. The distal adapter also adds functional attachment, or anchoring structure, for example, if a ring electrode (see FIGS. 8A and 8B) are wholly or partially disposed over the sensor package (including adapter portion 206). An advantage to a ring electrode wholly overlying the adapter portion of the package 200 is that the length of the sensor package can be reduced. An integrated circuit 201" adapted to at least of one of convey signals and calculate pressure applied to the membrane 201. The lead adapter 209 is designed to maintain alignment between the desired bending direction of the lead body and the axis of relative stiffness of the package.

Figure 5:
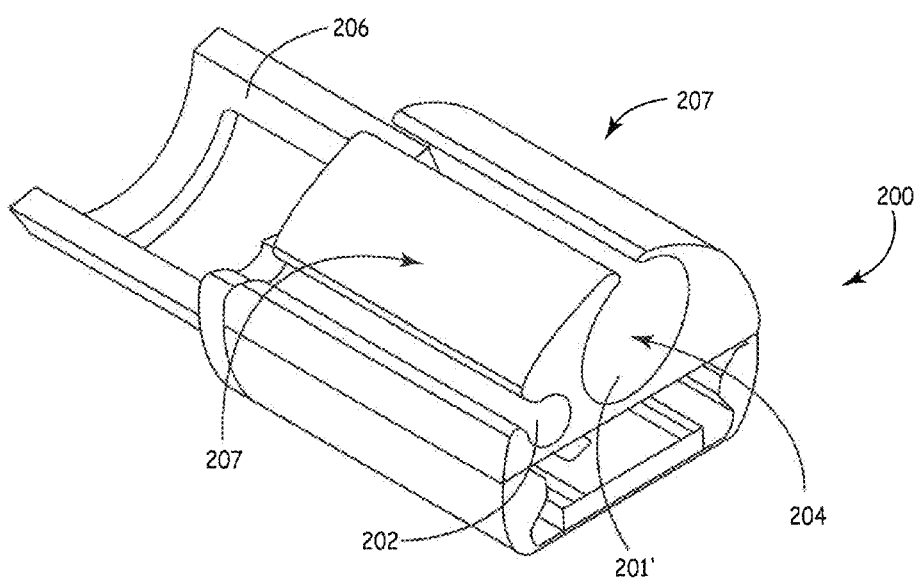
FIG. 5 is a perspective view illustrating the relatively thicker back portion of the sensor wherein the back portion has two longitudinal bores for receiving an elongated conductor and a torque coil, respectively.

FIG. 5 is a perspective view illustrating the relatively thicker back housing portion 207 of the sensor package 200 wherein the back housing portion 207 has two longitudinal bores 202,204 for receiving an elongated conductor to coupled to a distal ring electrode and a torque coil, respectively (not shown in FIG. 5). The bores 202,204 are depicted having an open longitudinal portion but such a portion is not required to practice the foregoing. In fact, the collar of the open portion of bores 202,204 can extend radially outward from a position approximately from the maximum diameter of each respective bore. A portion of the pressure sensor integrated circuit 201" is also depicted in FIG. 5 disposed within the package 200.

FIGS. 6A, 6B and 6C depict alternate views of the sensor package 200 depicted in FIGS. 4 and 5; namely, an elevational side view, a plan view and a cross-sectional view. The bores 202,204 of relatively thicker back portion 207 and the generally circular cross-sectional shape of the sensor 102 are depicted in FIG. 6C. The proximal and distal adapter 209,206 are also depicted. Whether or not the distal adapter 206 is bonded, seam welded (with a laser welder) or milled from a unitary portion of conductive material, it is considered to be part of the overall sensor package 200.

Figures 7A, 7B:
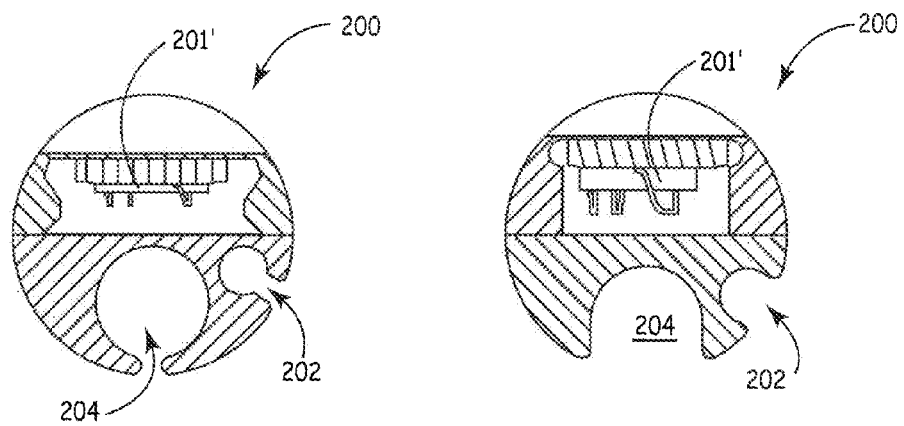
FIGS. 7A and 7B are elevational views of two related embodiments of the sensor package described and depicted herein.

FIGS. 7A and 7B are elevational views of two related embodiments of the sensor package described and depicted hereinabove. In essence the two depicted structures are very similar but nevertheless illustrate that besides one or both bores 202,204 being completely closed (as shown in FIG. 6C), one or both can be partially open (FIG. 7A) or substantially open (FIG. 7B). Also shown in FIGS. 7A and 7B, is the interior hermetic portion wherein the sensing circuitry 201' and sensor are coupled to the interior of the sensing membrane. Also illustrated is the fact that at least part of the sensor package 200 has a substantially circular cross section (e.g., at least the opposing end portions). Such a cross section, even if just partial, improves the ease and desirability of implanting such medical electrical leads by reducing changes in the overall diameter and shape of the lead.

FIGS. 8A and 8B are perspective views of an exemplary ring-type electrode 113 used for sensing and pacing and typically disposed distal of the sensor package 200. As shown in FIG. 8A, the interior of the ring electrode 113 has a groove 115 for receiving the distal end portion of the cable conductor 129. As depicted the ring electrode 113 resides on an electrically insulative flexible distal tip portion of the lead. However, assuming adequate electrical insulation disposed between the metallic sensor package 200 and the ring electrode 113, the ring electrode 113 could safely reside wholly, or partially, over a part of the sensor package 200. In a related aspect (and as depicted in FIG. 8B), the cable conductor if covered in insulation 130' and the torque coil is also covered with insulation 128. The latest embodiment have the advantage of further reducing the overall size of the sensor package, among other advantages.

The below narrative regarding the unitary, custom-molded insulative overlay for the conductive sensor package 200 utilizes reference numerals corresponding to the structures recited below from various drawings (e.g., see FIG. 1 at 102 and 201 for the overlay). The sensor package 200 is wholly surrounded by a custom-molded insulative overlay, including the sensing membrane 201 or diaphragm. The following narrative describes the overlay and the simple manner of fabrication and attachment, which is a vast improvement over prior art techniques of rendering a conductive sensor package electrically neutral.

The silicone sensor overlay electrically isolates the sensor housing 200 from the lead body and provides a uniform layer of insulation over the sensor diaphragm 201 in order to maintain a consistent interface between the blood and the sensor capsule 200 since motion of the diaphragm 201 is translated into pressure difference. This overlay is also necessary to prevent any artifacts from the pacing pulse from interfering with the pressure signal. It is bonded to the flexible distal (tip-to-ring) spacer 110 at one side of the capsule 200 and the lead body tubing 104 at the other side providing strength and sealing of the capsule 200. The inside of the overlay is the same shape as the capsule providing a conformal fit and when backfilled with silicone medical adhesive provides adhesion and intimate contact with the sensor and the overlay allowing the overlay to move with the sensor diaphragm. The overlay is on the order of 0.004 to 0.006 in thickness.

The overlay is molded in a liquid silicone molding press by injecting a two-part liquid silicone rubber into a mold whose core pin is shaped identically to the outside surface of the sensor including the recessed diaphragm 201. This rubber is vulcanized in the heated mold until it is cured and then removed from the core pin. The overlay is then post-cured to fully cure the part and then inspected and any loose flash removed.

At final assembly the overlay is swelled in a suitable solvent (e.g., heptane) in order to position it over the assembled sensor capsule 200. The overlay is allowed to dry to its original shape and then a small amount of silicone medical adhesive is dispensed under the overlay around the sensor circumference and also to the adjoining parts and allowed to dry. This design and method of manufacture saves significant amount of time and cost versus previous methods of coating a conductive sensor package and also offers acceptable pressure sensing performance.

It will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention. For example, the sensor could comprise an accelerometer (single- or multi-axis) which for any of a number of reasons might need to have reduced structure on one or more sides thereof thus becoming susceptible to the objects solved herein.

The invention claimed is:

1. A medical electrical lead, comprising:
    an elongated lead body formed of a biocompatible material having at least two longitudinal lumens formed in the lead body;
    an elongated metallic torque coil disposed within a first lumen of the lead body;
    an elongated metallic cable disposed within a second lumen of the lead body; and
    a conductive hermetic sensor package coupled to the lead body including a first means for securing a portion of the metallic torque coil and a separate second means for securing a portion of the elongated metallic cable longitudinally through a portion of the conductive hermetic sensor package,
    wherein the first means for securing the portion of the metallic torque coil and the second means for securing the portion of the elongated metallic cable are conductive and are integrally formed in the conductive hermetic sensor package.

2. A lead according to claim 1, wherein the first means for securing the portion of the metallic torque coil and the second means for securing the portion of the elongated metallic cable comprise a pair of bores substantially aligned with the longitudinal axis of the lead body.

3. A lead according to claim 2, wherein the pair of bores comprises at least one open-sided bore.

4. A lead according to claim 1, wherein the sensor package is fabricated of one of a titanium alloy and titanium, and the first means for securing the portion of the metallic torque coil and the second means for securing the portion of the elongated metallic cable are formed in the at least one of the titanium alloy and titanium.

5. A lead according to claim 1, further comprising electrical insulation disposed between the first means for securing and the torque coil and between the second means for securing and the elongated cable.

6. A lead according to claim 5, wherein the electrical insulation is at least one of disposed or formed on the first and second means for securing.

7. A lead according to claim 1, further comprising a ring-type electrode coupled distal of the sensor package, wherein the ring-type electrode couples to the elongated metallic cable.

8. A lead according to claim 7, further comprising a tip-type electrode coupled distal to the ring-type electrode, wherein the metallic helix tip electrode couples to the elongated metallic torque coil.

9. A lead according to claim 8, further comprising a relatively flexible elongated member coupled distal of the sensor package and wherein the tip-type electrode couples to the distal end of said elongated member.

10. A lead according to claim 8, further comprising a custom-molded, unitary silicone overlay disposed over the entire exterior surface of the sensor package.

11. A lead according to claim 1, wherein the physiologic sensor comprises one of a pressure sensor having a deflectable sensing face portion and an accelerometer.

12. A lead according to claim 1, wherein opposing end portions of the sensor package have a substantially circular axial cross-section.

13. A lead according to claim 1, wherein the sensor package includes an integrated distal adapter member and further comprising a ring-type electrode one of wholly and partially overlying the integrated distal adapter member.

14. A medical electrical lead, comprising:
    an elongated lead body formed of a biocompatible material having at least two longitudinal lumens formed in the lead body;
    a metallic torque coil disposed within a first lumen of the lead body;
    a metallic cable disposed within a second lumen of the lead body;
    a conductive, hermetic sensor package system coupled to the lead body including a deflectable member sensitive to a physiologic variable of a subject, and a pair of spaced apart conductive bypass structures for securing a portion of the metallic torque coil and a portion of the metallic cable longitudinally through a portion of the sensor package,
        wherein the pair of spaced apart bypass structures are conductive and are integrally formed in the conductive hermetic sensor package; and
    electrical insulation disposed between the conductive bypass structures and the torque coil and the metallic cable.

15. A lead according to claim 14, wherein the deflectable member comprises one of a deflectable membrane, a deflectable diaphragm, an accelerometer.

16. A lead according to claim 14, wherein the sensor package includes a distal adapter member and further comprising a ring-type electrode one of wholly and partially overlying the distal adapter member.

17. A lead according to claim 16, further comprising:
    a customized, unitary silicone overlay disposed over the entire exterior surface of the sensor package.

18. A lead according to claim 14, wherein the electrical insulation is at least one of disposed or formed on the pair of conductive bypass structures.

19. A medical electrical lead, comprising:
an elongated lead body formed of a biocompatible material having at least two longitudinal lumens formed in the lead body;
an elongated metallic torque coil within a first lumen of the lead body;
an elongated metallic cable within a second lumen of the lead body;
means for coupling a hermetic conductive sensor package to the lead body, wherein the sensor package includes a deflectable member sensitive to a physiologic variable of a subject and a pair of conductive bypass structures longitudinally through the sensor package, wherein the pair of bypass structures are integrally formed into the hermetic conductive sensor package; and
means for electrically insulating each of the pair of conductive bypass structures from the torque coil and the metallic cable, respectively.

20. A lead according to claim 19, further comprising:
a customized, unitary silicone overlay disposed over the entire exterior surface of the sensor package.

21. A lead according to claim 20, further comprising a ring-type electrode one of wholly and partially overlying the sensor package and disposed near a distal edge portion of the customized, unitary silicone overlay.

22. A lead according to claim 19, wherein the means for electrically insulating each of the pair of conductive bypass structures is at least one of disposed or formed on the pair of conductive bypass structures.

* * * * *